US010235861B1

(12) United States Patent
Burns et al.

(10) Patent No.: US 10,235,861 B1
(45) Date of Patent: Mar. 19, 2019

(54) MONITORING A DISINFECTED STATE OF A MOBILE DEVICE

(71) Applicant: Metrex Research, LLC, Orange, CA (US)

(72) Inventors: Steven Burns, Marina del Rey, CA (US); Abhigyan Som, Brea, CA (US); Tuyen Quang Nguyen, Buena Park, CA (US)

(73) Assignee: METREX RESEARCH, LLC, Orange, CA (US)

( * ) Notice: Subject to any disclaimer, the term of this patent is extended or adjusted under 35 U.S.C. 154(b) by 0 days.

(21) Appl. No.: 15/864,910

(22) Filed: Jan. 8, 2018

(51) Int. Cl.
*G08B 21/18* (2006.01)
*G04F 1/00* (2006.01)
*G01P 13/00* (2006.01)
*G08B 21/02* (2006.01)
*G06F 3/0488* (2013.01)

(52) U.S. Cl.
CPC ............ *G08B 21/182* (2013.01); *G01P 13/00* (2013.01); *G04F 1/005* (2013.01); *G08B 21/02* (2013.01); *G06F 3/0488* (2013.01)

(58) Field of Classification Search
CPC .... A61B 2560/0242; A61B 2562/0219; A61B 5/01; A61B 5/1101; A61B 5/14532; A61B 5/6824; A61B 5/6826; A61B 5/6843; A61B 5/7282
USPC ........................................................ 340/540
See application file for complete search history.

(56) References Cited

U.S. PATENT DOCUMENTS

| 7,557,312 B2 | 7/2009 | Clark et al. |
| 7,718,395 B2 | 5/2010 | Carling |
| 7,780,453 B2 | 8/2010 | Carling |
| 8,264,470 B2 | 9/2012 | Sakurai |
| 8,816,856 B2 | 8/2014 | Whitehouse et al. |
| 9,069,390 B2 | 6/2015 | Marsden et al. |
| 9,170,205 B2 | 10/2015 | Burns et al. |
| 9,623,130 B2 | 4/2017 | Tumanov |

(Continued)

FOREIGN PATENT DOCUMENTS

EP 3043244 7/2016

OTHER PUBLICATIONS

Rutala et al., "Bacterial Contamination of Keyboards: Efficacy and Functional Impact of Disinfectants," article, Infection Control and Hospital Epidemiology (Apr. 2006) Volumn 27, Issue 4, pp. 372-377.

(Continued)

*Primary Examiner* — Ojiako K Nwugo
(74) *Attorney, Agent, or Firm* — Michael Best & Friedrich LLP

(57) ABSTRACT

A mobile device that includes an input device, an output device, and an electronic processor connected to the input device and the output device. The electronic processor is configured to receive, from the input device, information about a disinfectant and set a threshold time, a threshold activity level, or both the threshold time and the threshold activity level based on the information about the disinfectant. The electronic processor is also configured to track a passage of time, an activity level, or both. If the passage of time is greater than or equal to the threshold time, the activity level is greater than or equal to the threshold activity level, or both then the electronic processor is configured to output a user notification, via the output device.

32 Claims, 9 Drawing Sheets

(56) References Cited

U.S. PATENT DOCUMENTS

| | | | | |
|---|---|---|---|---|
| 2008/0246599 | A1* | 10/2008 | Hufton | G01S 1/70 340/529 |
| 2010/0117836 | A1* | 5/2010 | Seyed Momen | G01S 1/70 340/573.1 |
| 2012/0116803 | A1* | 5/2012 | Reid | A61L 2/28 705/2 |
| 2012/0173274 | A1* | 7/2012 | Rensvold | G16H 40/20 705/2 |
| 2013/0115132 | A1* | 5/2013 | Engimann | A61L 2/16 422/28 |
| 2014/0375431 | A1* | 12/2014 | Cristache | G01S 13/876 340/10.1 |
| 2015/0090903 | A1* | 4/2015 | Cole | A61L 2/10 250/492.1 |
| 2015/0090904 | A1* | 4/2015 | Cole | A61L 2/10 250/492.1 |
| 2015/0258228 | A1* | 9/2015 | Cohen | A61L 2/10 345/178 |

OTHER PUBLICATIONS

Burns et al., "Pushing Our Buttons: How Many Cycles Does It Take to Remove an Active Disinfecting Compound from a Keypad?," article (2014) vol. 42, Issue 6, Supplement, pp. S39-S40.
Wikipedia, "Unique Device Identification," [This page was last edited on Sep. 27, 2016] 2 pages, https://en.wikipedia.org/wiki/Unique_Device_Identification.
Carling, "Methods for assessing the adequacy of practice and improving room disinfection," article American Journal of Infection Control 41 (2013) pp. S20-S25.

* cited by examiner

MONITORING A DISINFECTED STATE OF A MOBILE DEVICE

FIELD

Embodiments relate to monitoring a disinfected state of a mobile device.

BACKGROUND

Mobile computing devices, for example, smartphones, tablets, and similar devices are increasingly being used in the medical field. However, buttons, touch screens, and other surfaces can become contaminated from dirt and pathogens (for example, bacteria, viruses, and other microorganisms) present on the hands of users. In a medical environment, contaminated equipment can spread disease.

SUMMARY

While there is a general recognition that mobile devices may act as carriers of pathogens, most efforts to disinfect mobile devices rely on simple, unreliable manual procedures where a disinfectant is wiped on or otherwise applied to the device whenever the user remembers to do so. For example, in some medical facilities, a personnel procedure is established so that a mobile device is disinfected every time healthcare personnel enters and/or leaves a patient or procedure room in a medical facility.

Generally, human beings struggle to reliably follow established procedures and/or track information such as the number of times a mobile device has been touched and how long it has been since the mobile device was disinfected. Depending on personnel to disinfect the mobile device is unreliable and not practical. Compliance rates by hospital workers are very low, often less than 50%, which increases cross contamination risk. Further, even if the established procedure was complied with, if a device is disinfected and then not handled by personnel, the device may be disinfected (for example, undergo an application of disinfectant) needlessly.

Prior-art approaches for monitoring the disinfection status of a mobile device rely on an approach that is too simplistic and does not consider the whole picture. Once a device is touched, it is assumed that the device is infected (or not disinfected). For example, in prior approaches a mobile device is assumed to be infected once the surface (for example, a touchscreen) of the mobile device has been touched.

But the prior-art approaches ignore that disinfection is based on the probability that there is enough disinfectant on an area of a surface for the disinfectant to be detectable or to kill a pathogen. Complex algorithms can be used to calculate a confidence level that a certain percentage of a disinfectant is present. Unlike the prior-art approaches, the new technology disclosed herein uses a persistence claim of a disinfectant to determine the confidence level and probability that a percent of the disinfectant is sufficiently present on the mobile device and, therefore, whether the mobile device is truly infected or disinfected. By utilizing the persistence claim of the disinfectant, the time between disinfections of the mobile device may be increased, and more accurate information can be relayed to the user. The persistence claim of the disinfectant is determined based on various factors unique to the disinfectant, such as how much time passes before the disinfectant is not detected on a surface and the number of times the same area of a surface can be touched before the disinfectant is not detected on that area of the surface.

In some embodiments, the mobile device receives the persistence claim of the disinfectant by scanning a unique device identifier or a quick response code, which can include information relating to certain threshold levels such as time and/or activity level. The mobile device and method described herein track a time that has passed since the mobile device was last disinfected and a change in an activity level of the mobile device since the mobile device was last disinfected. The activity level may be measured in a number of ways, including for example, activity on a touch screen, activation of the display (whether the screen is lit or dark), or a physical interaction between a user and the touch screen. If the time reaches the threshold time or the activity level reaches the threshold activity level the mobile device outputs a user notification until the mobile device is disinfected.

One embodiment provides a mobile device that includes an input device, an output device, and an electronic processor connected to the input device and the output device. The electronic processor is configured to receive, from the input device, information about a disinfectant and set a threshold time, a threshold activity level, or both the threshold time and the threshold activity level based on the information about the disinfectant. The electronic processor is also configured to track a passage of time, an activity level, or both. If the passage of time is greater than or equal to the threshold time, the activity level is greater than or equal to the threshold activity level, or both then the electronic processor is configured to output a user notification, via the output device.

Another embodiment provides a method for monitoring a disinfection status of a mobile device. The method includes receiving information about a disinfectant from an input device and setting, with an electronic processor, a threshold time, a threshold activity level, or both the threshold time and the threshold activity level, based on the received information about the disinfectant. The method also includes tracking, with the electronic processor, a passage of time, an activity level, or both, and outputting a user notification from an output device if the passage of time is greater than or equal to the threshold time, the activity level is greater than or equal to the threshold activity level, or both.

Other aspects will become apparent by consideration of the detailed description and accompanying drawings.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
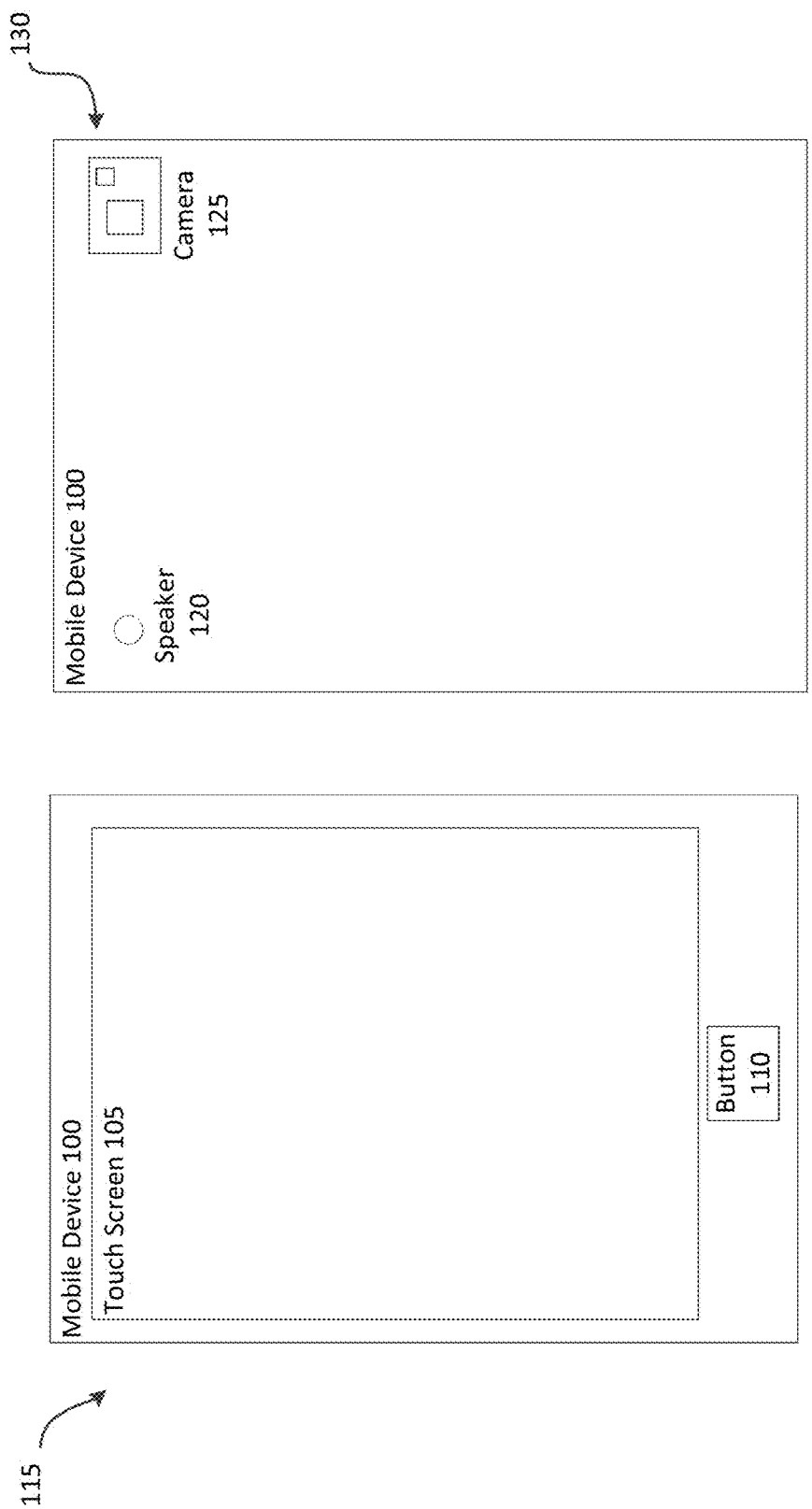
FIG. 1 is a diagram of a mobile device.

FIG. 1 illustrates a mobile device 100. In the embodiment illustrated, the mobile device 100 includes a touch screen 105 and a button 110 located on a first side 115 of the mobile device 100. The mobile device 100 also includes a speaker 120 and a camera 125 that are located on a second side 130 of the mobile device 100. The embodiment illustrated in FIG. 1 provides but one example of the components of the mobile device 100. In some embodiments, the mobile device 100 includes additional, fewer, or different components. For example, there may be additional buttons located on the mobile device 100 or the mobile device 100 may not include the camera 125. The components of the mobile device 100 may have positions on the mobile device 100 other than the positions illustrated in FIG. 1. For example, the camera 125 may be located on the first side 115 of the mobile device 100 rather than the second side 130 of the mobile device 100.

Figure 2:
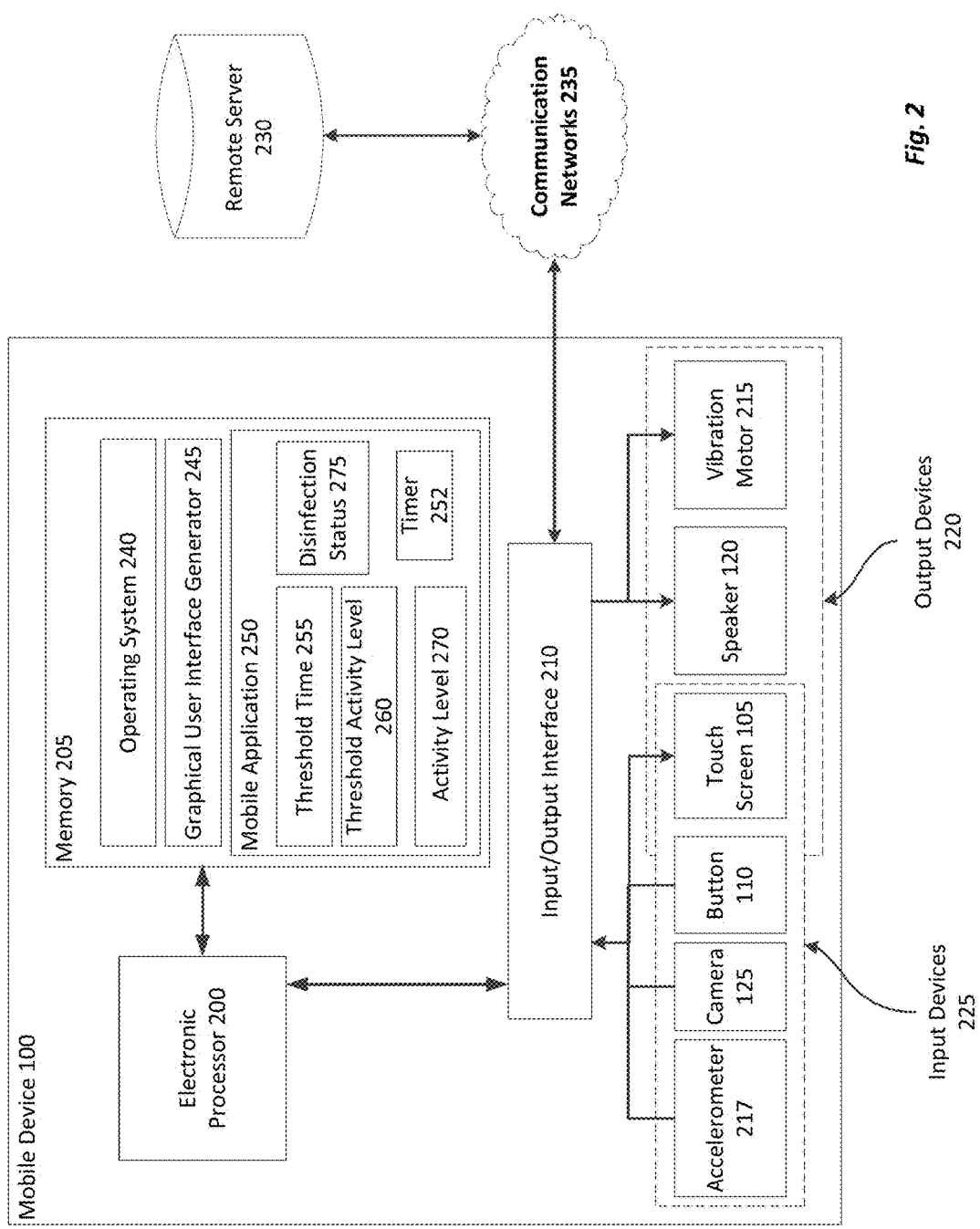
FIG. 2 includes a block diagram of internal components of the mobile device of FIG. 1 and an illustration of network resources external to the mobile device.

FIG. 2 illustrates, among other things, internal components of the mobile device 100. The mobile device 100 includes a plurality of electrical and electronic components that provide power, operational control, and protection to the components and modules within the mobile device 100. The mobile device 100 includes, among other things, an electronic processor 200 (such as a programmable electronic microprocessor, microcontroller, or similar device), a memory 205 (for example, non-transitory, machine readable memory), and an input/output interface 210. The electronic processor 200 is communicatively connected to the memory 205 and the input/output interface 210.

In the example illustrated, the input/output interface 210 allows several components including the camera 125, the touch screen 105, the button 110, the speaker 120, a vibration motor 215, and an accelerometer 217 to communicate with the electronic processor 200. In some instances, the touch screen 105, speaker 120, and vibration motor 215 function as output devices 220. In some instances, the touch screen 105, button 110, camera 125, and accelerometer 217 function as input devices 225. The components of the mobile device 100 may be of various constructions and may use various communication types and protocols.

In one example, the mobile device 100 communicates with a remote server 230. The remote server 230 and the mobile device 100 communicate over one or more wired or wireless communication networks 235. Portions of the communication networks 235 may be implemented using a wide area network, such as the Internet, a local area network, such as a Wi-Fi or Bluetooth™ network, and combinations or derivatives thereof. It should be understood that the remote server 230 may perform additional functionality other than the functionality described in the present application. For example, as noted above, in some embodiments, the functionality described herein as being performed by the remote server 230 may be distributed among multiple devices, such as multiple servers operated within a cloud environment.

In some embodiments, the electronic processor 200 executes instructions stored in the memory 205. The memory 205 includes several software components including an operating system 240, a graphical user interface generator 245, and a mobile application 250. The mobile application 250 is a software application executable by the electronic processor 200. In one example, the mobile application 250 contains a timer 252 or a similar mechanism that can track a passage of time. In the example provided, the mobile application 250 also contains a plurality of variables, including a threshold time 255, a threshold activity level 260, an activity level 270, and a disinfection status 275. The operation of the mobile device 100 is described in greater detail below in relation to the methods described herein.

Figure 3:
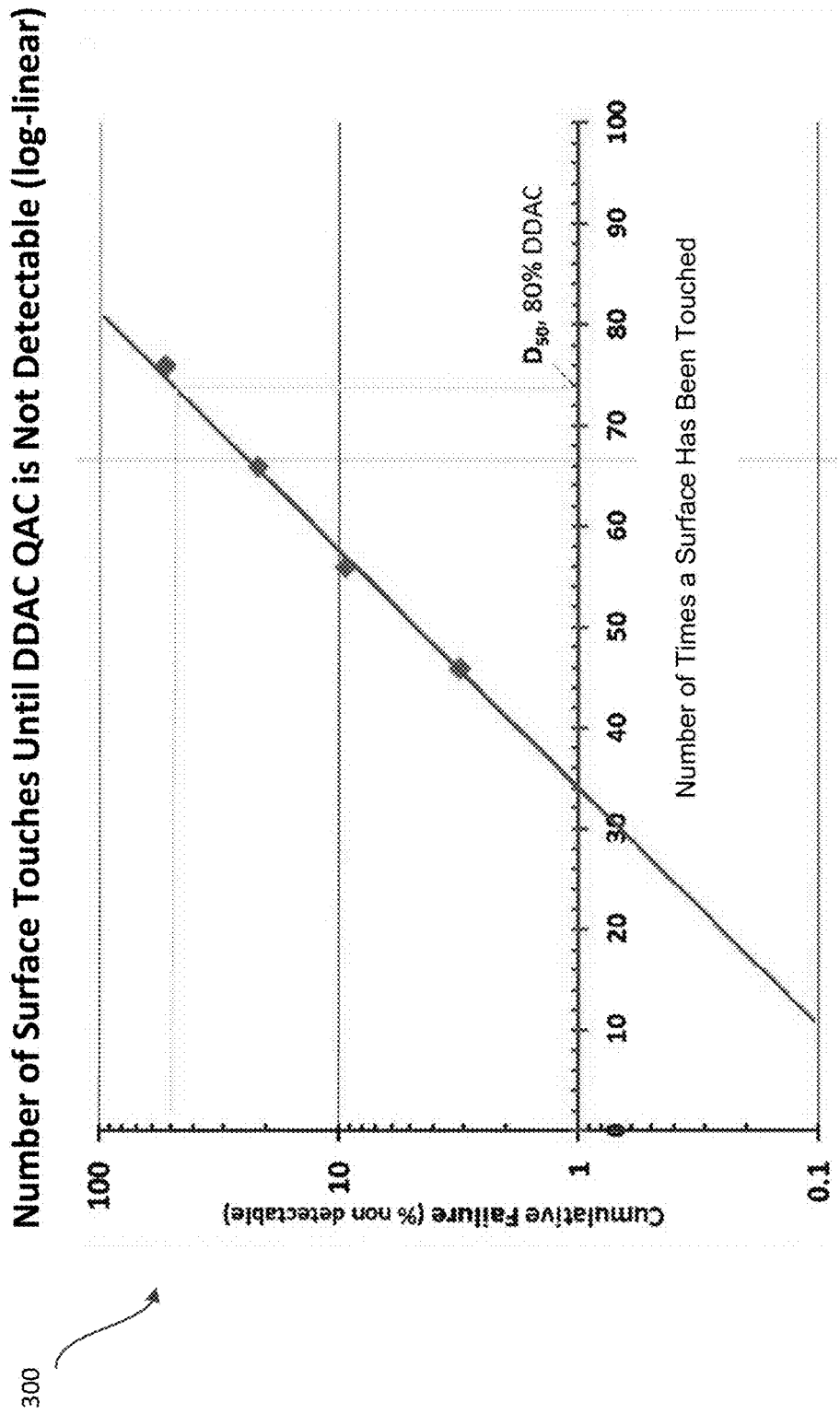
FIG. 3 is a graph illustrating the dissipation of disinfectant from a surface as the number of times that the surface is touched increases.

FIG. 3 is a graph 300 illustrating a rate of dissipation of a disinfectant from a surface as the number of times that the surface has been touched increases. As illustrated by the graph 300, the disinfectant applied to a surface is able to kill microorganisms after the surface has been touched. The ability of the disinfectant to kill microorganisms after the disinfectant has been applied to a surface, for example, the touch screen 105, is sometimes referred to as a "persistence claim" of the disinfectant. A discussion related to persistence claims or sustained disinfectant efficacy is found in Rutala, White, Gergen, and Weber, Bacterial Contamination of Keyboards: Efficacy and Functional Impact of Disinfectants, Infection Control & Hospital Epidemiology 27 (2006): 372-377. The persistence claim of the disinfectant is based on a time period that the disinfectant is detectable on the surface and a number of times the surface can be touched before the disinfectant on the surface is undetectable (pursuant to accepted scientific techniques).

In the example provided, the graph 300 shows the number of times a surface that has had didecyldimethylammonium chloride (DDAC) applied to it can be touched before the DDAC is no longer detected. DDAC is a Quaternary Ammonium Compound (QAC) disinfectant. QACs kill a wide variety of microorganisms. QACs are odorless, colorless, and non-corrosive making them highly suitable for disinfecting surfaces. The x-axis of the graph 300 represents the number of times a surface has been touched. The y-axis of the graph 300 illustrates the percent of the DDAC on the surface that is not detected.

Disinfection is based on the probability that there is enough disinfectant on an area of a surface, such as a touch screen, for the disinfectant to be detectable or to kill a pathogen. Studies (for example, the study whose results are depicted in the graph illustrated by FIG. 3) demonstrate that it is possible to use an algorithm to determine the probability that a disinfectant is detectable on a surface after a certain number of touches. These algorithms calculate a confidence level that a certain percentage of the disinfectant is present. For example, the graph 300 shows that there is a fifty percent probability (the confidence level) that the DDAC on the surface is eighty percent undetected once the surface has been touched 74 times. By calculating the confidence level that a certain percentage of the disinfectant is present on a surface using test methods recognized by the scientific community, the embodiments described herein provide a more accurate method for monitoring a disinfected state of a mobile device than prior methods for monitoring a disinfected state of a mobile device.

It should be understood that disinfectants other than DDAC may be applied to the surface. Thus, embodiments are not limited to the use of DDAC. In addition, other disinfectants may have the same persistence claim as DDAC or different persistence claims than DDAC and other embodiments of the invention may be adjusted to account for these differences, for example, by adjusting touch counts, time thresholds, or both. Other disinfectants that may be used include other QACs, such as benzalkonium chloride, benzethonium chloride, methylbenzethonium chloride, cetalkonium chloride, cetylpyridinium chloride, cetrimonium chloride, cetrimonium bromide, dofanium chloride, and domiphen bromide. Non-QAC disinfectants may also be used. Combinations of disinfectants may also be used.

The disinfectants may have broad spectrum activity against a variety of microorganisms. For example, the disinfectant may have bactericidal, virucidal, and/or fungicidal activity. The disinfectant may be effective against bacteria including *Staphylococcus* species such as *Staphylococcus aureus* (including resistant strains such as methicillin-resistant *Staphylococcus aureus* and oxacillin-resistant *Staphylococcus aureus*), *Escherichia coli*, *Clostridium difficile*, *Pseudomonas aeruginosa*, *Salmonella enterica*, *Enterococcus* species (including resistant species such as Vancomycin Resistant *Enterococcus faecalis*), *Bacillus* species, *Micrococcus* species, *Streptococcus* species, or any combination thereof. The disinfectant may be effective against viruses such as hepatitis B virus (HBV), hepatitis C Virus (HCV), herpes simplex virus types 1 and 2, human immunodeficiency virus (HIV-1), respiratory syncytial virus (RSV), and norovirus. The disinfectant may be effective against fungi such as *Trichophyton mentagrophytes*.

The disinfectant may be applied to the surface as part of a formulation using an applicator or a wipe. The formulation may include other components that are optically clear, so as to avoid loss of clarity.

Figure 4:
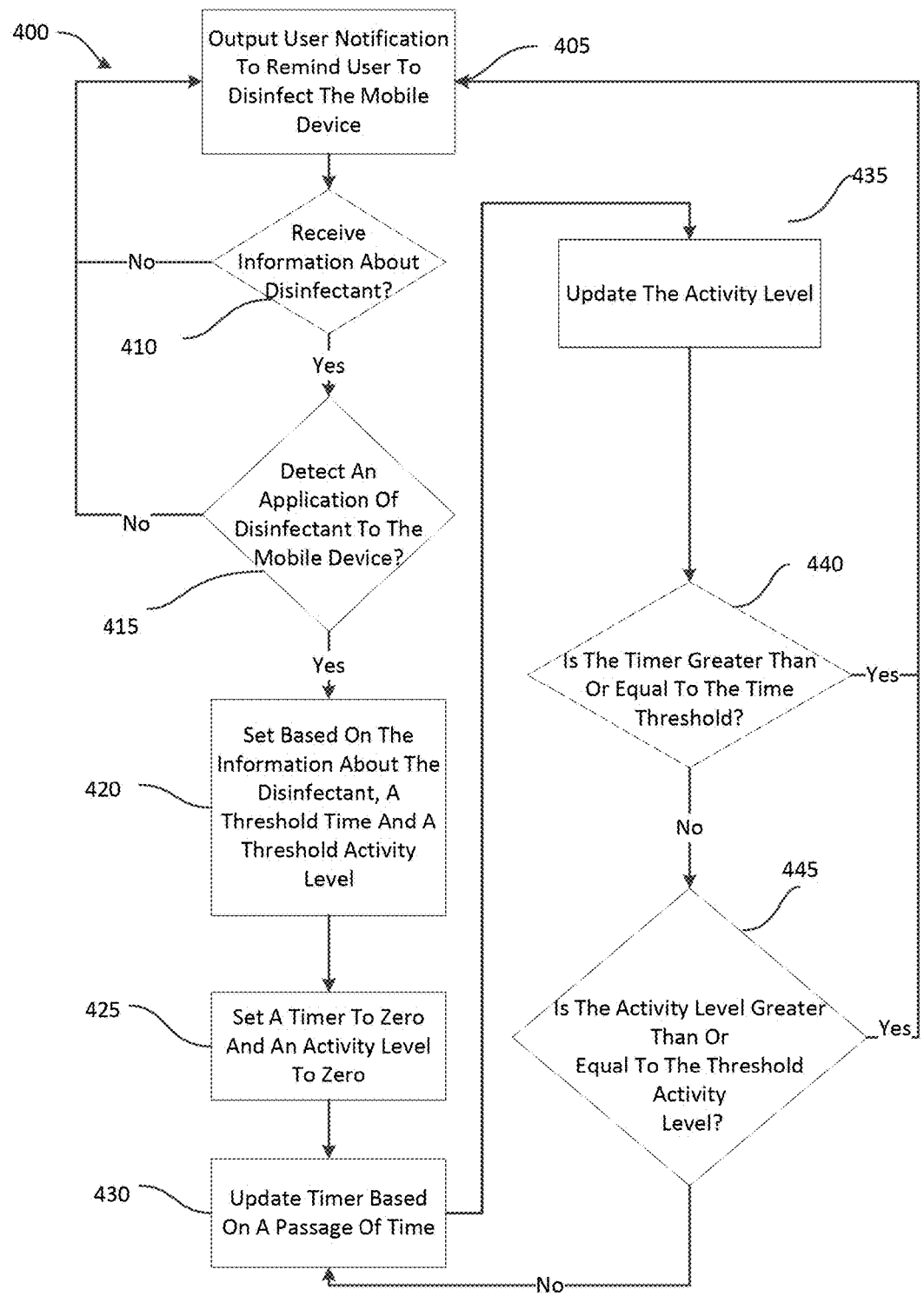
FIG. 4 is a flowchart of a method for maintaining a disinfection status of a mobile device.

FIG. 4 is a flowchart of a method 400 for maintaining a disinfected status of a mobile device. The electronic processor 200 outputs, via at least one of the output devices 220, a user notification to remind a user to disinfect the mobile device 100 (block 405). In one embodiment of the method 400, the user notification is aural, for example, a beep or a voice message, which emanates from the speaker 120. In other embodiments, the user notification is visual, for example, text in a dialog box displayed on the touch screen 105, haptic, for example, a vibration caused by the vibration motor 215, or a combination of aural, visual, or haptic notifications. The electronic processor 200 outputs, via at least one of the output devices 220, the user notification (for example, periodically) until the electronic processor 200 receives information about a disinfectant (block 410) and, in some embodiments, detects an application of disinfectant (block 415). In some embodiments, the electronic processor 200 receives the information about the disinfectant via the touch screen 105 (for example, via user input received from an entry in a dialog box displayed as part of a graphical user interface). In other embodiments, the electronic processor 200 receives the information about the disinfectant via the camera 125, for example, via capture of an image containing a quick response (QR) code or a barcode. In some instances, a graphical code in the form of unique device identifier (UDI) is used. In the United States, UDI are part of an FDA system for tracking regulated medical devices. More information on unique device identification can be found at: https://en.wikipedia.org/wiki/Unique_Device_Identification. In other instances, the mobile device 100 includes a radio frequency (RF) reader (not shown) and the electronic processor 200 receives information about the disinfectant by reading information from an RF tag. In some instances, the codes or tags are encoded with information about the disinfectant that includes, for example, an identification of the disinfectant, the persistence claim of the disinfectant, the threshold time 255, and the threshold activity level 260. In some embodiments, the electronic processor 200 detects the application of disinfectant (block 415) by receiving a signal from the touch screen 105 that a predetermined portion of the surface area of the touch screen 105 has been touched within a predetermined amount of time of receiving the information about the disinfectant. In some embodiments, the electronic processor 200 also prompts the user to confirm the application of the disinfectant, for example, by displaying a prompt on the touch screen 105, receiving a response from the touch screen 105 based on user input, or by generating an audible prompt and receiving a response based on a voice input from a microphone. It should be understood that other methods of detecting the application of the disinfectant may be used by the mobile device 100. It should also be understood that the method used to detect the application of the disinfectant may depend upon the received information about the disinfectant.

If the persistence claim of the disinfectant is not included in the information about the disinfectant then, upon receiving the information about the disinfectant, the electronic processor 200 retrieves the persistence claim associated with the disinfectant from a lookup table stored in memory 205 or from the another source, for example, the remote server 230. If the electronic processor 200 is unable to retrieve the persistence claim associated with the disinfectant, the electronic processor 200 outputs an error message, for example, in a dialog box displayed on the touch screen 105. If the threshold time 255 and the threshold activity level 260 were not included in the received information about the disinfectant, the electronic processor 200 sets the threshold time 255 and the threshold activity level 260 based on the persistence claim of the disinfectant (block 420). The threshold values (threshold time and threshold activity level) depend on the type of disinfectant, and the efficacy of the threshold values for killing pathogens has been validated.

In some embodiments, the electronic processor 200 adjusts the threshold time 255 and the threshold activity level 260 based on the number and type of software applications stored in the memory 205 of the mobile device 100. The electronic processor 200 also uses the information about the disinfectant to determine if the disinfectant is compliant with regulatory standards, for example, the regulatory standards set by the environmental protection agency. If the disinfectant does not meet the regulatory standards the electronic processor 200 outputs an error message such as the following: "Disinfectant does not meet regulatory standards. Please provide another disinfectant." The error message is presented in, for example, a dialog box displayed on the touch screen 105. In some embodiments, when the disinfectant does not meet the regulatory standards, the electronic processor 200 requires that it receive information about a different disinfectant before permitting the mobile application 250 to proceed to additional processing, for example, detecting the application of disinfectant.

In those embodiments where detection is implemented, upon detecting the application of disinfectant, the electronic processor 200 sets the timer 252 to zero and the activity level 270 to zero (block 425). In other embodiments, the electronic processor 200 sets the timer 252 to zero and the activity level 270 to zero upon receiving the information about the disinfectant. After the timer 252 is set, the electronic processor 200 updates the timer 252 based on the passage of time (block 430). As described in further detail below, the electronic processor 200 updates the activity level 270 when it detects that the mobile device 100 is in use (block 435). In some embodiments, the electronic processor 200 outputs a user notification (for example, a small graphic of a gauge) on the touch screen 105 to inform the user how much of the disinfectant has dissipated from the touch screen 105. If the timer 252 is greater than or equal to the threshold time 255 (block 440) the electronic processor 200 outputs the user notification (for example, periodically), via at least one of the output devices 220 (block 405). If the activity level 270 is greater than or equal to the threshold activity level 260 (block 445) the electronic processor 200 outputs the user notification (for example, periodically), via at least one of the output devices 220 (block 405).

In an alternative example, in those embodiments where detection is implemented, upon detecting the application of disinfectant, the electronic processor 200 stores in memory 205 a value of the timer 252 and a value of the activity level 270. After the value of the timer 252 is stored in memory 205, the electronic processor 200 updates the timer 252 based on the passage of time (block 430). As described in further detail below, the electronic processor 200 updates the activity level 270 when it detects that the mobile device 100 is in use (block 435). The electronic processor 200 calculates a difference between the value of the timer 252 stored in memory 205 and a current value of the timer 252. If the difference is greater than or equal to the threshold time 255 the electronic processor 200 outputs the user notification (for example, periodically), via at least one of the output devices 220 (block 405). The electronic processor 200 also calculates a difference between the value of the activity level 270 stored in memory 205 and a current value of the activity level 270. If the difference is greater than or equal to the threshold activity level 260 the electronic processor 200 outputs the user notification (for example, periodically), via at least one of the output devices 220 (block 405).

The activity level 270 is a measure of whether the mobile device 100 is in use. In one example, the electronic processor 200 measures whether the mobile device 100 is in use by tracking a time (or amount of time) that the touch screen 105 is active, a time or whether the accelerometer 217 outputs a value greater than zero, or both the touch screen 105 is active and the accelerometer 217 outputs a value greater than zero. The touch screen 105 is assumed to be "active" when the touch screen 105 is lit (as opposed to being in a darkened state). When the time that the mobile device 100 is in use is greater than or equal to a threshold time, the threshold activity level 260 is met (block 445). The electronic processor 200 then outputs the user notification (for example, periodically) via at least one of the output devices 220 (block 405).

In other embodiments, the activity level 270 is a counter for a number of screen touches and the threshold activity level 260 is a number of screen touches. The number of screen touches provides the electronic processor information on the removal of disinfectant, the addition of potential contamination, or both. The electronic processor 200 updates the counter for the number of screen touches when it detects that the touch screen 105 is touched. When the counter for number of screen touches is greater than or equal to the number of screen touches (block 415), the electronic processor 200 outputs the user notification via at least one of the output devices 220 (block 405).

In some instances, the mobile device 100 may have a plurality of counters for the number of screen touches. Each of the plurality of counters for the number of screen touches is associated with an area of the touch screen 105. Every time an area of the touch screen 105 is touched the counter for the number of screen touches that is associated with the touched area is updated. Each counter for the number of screen touches is compared to the number of screen touches. If one or more counters for the number of screen touches is greater than or equal to the number of screen touches the threshold activity level 260 is met (block 445) and the electronic processor 200 then outputs the user notification (for example, periodically) via at least one of the output devices 220 (block 405). Assigning separate counters for the number of screen touches to different areas of the touch screen 105 may extend the time between applications of disinfectant to the mobile device 100 and provide a more accurate representation of the disinfection status 275 of the mobile device 100.

In some embodiments, the electronic processor 200 sets the disinfection status 275 of the mobile device 100 to disinfected when the electronic processor 200 receives information about the disinfectant. In other embodiments, the electronic processor 200 sets the disinfection status 275 of the mobile device 100 to disinfected when the electronic processor 200 receives information about the disinfectant and detects the application of disinfectant. The electronic processor 200 sets the disinfection status 275 of the mobile device 100 to not disinfected if the timer 252 is greater than or equal to the threshold time 255. The electronic processor 200 also sets the disinfection status 275 of the mobile device 100 to not disinfected if the activity level 270 is greater than or equal to the threshold activity level 260.

Figure 5:
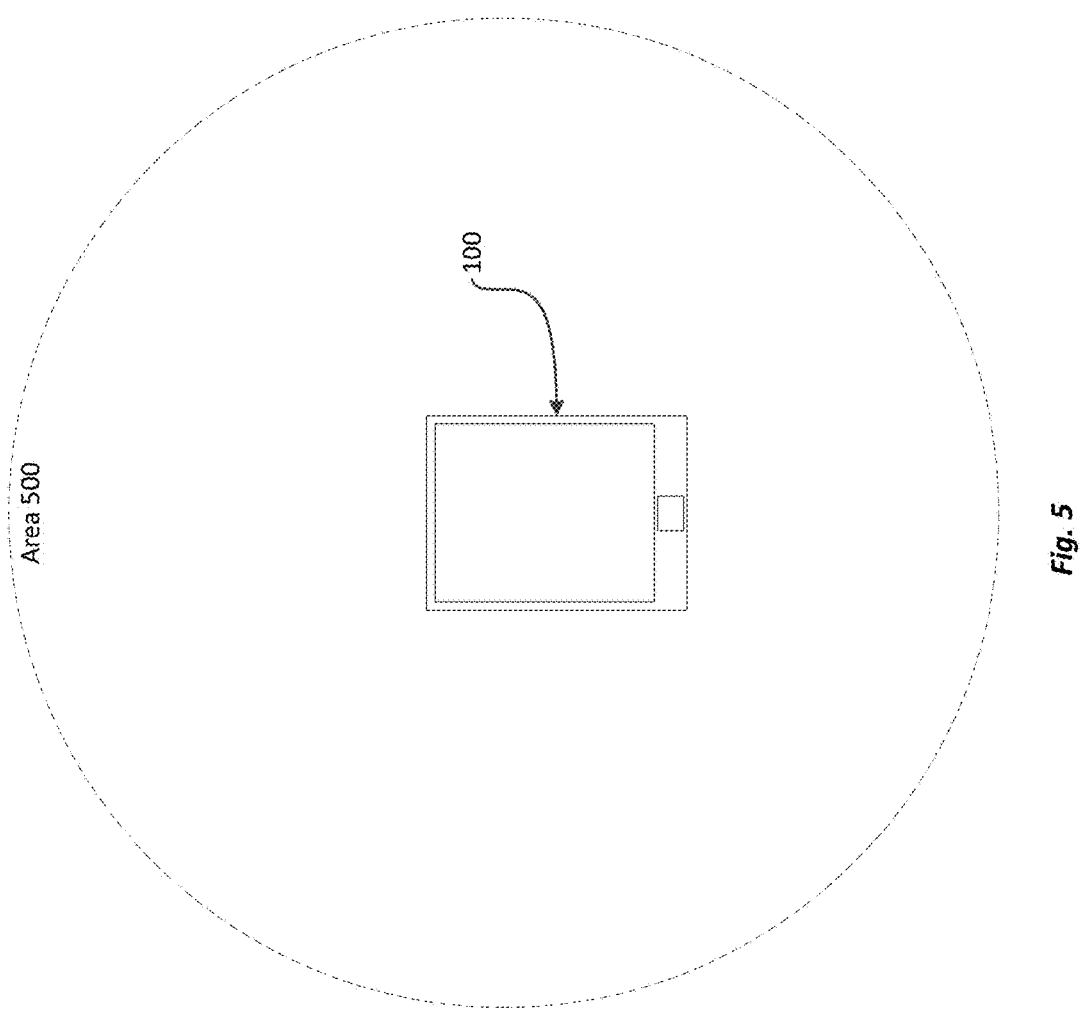
FIG. 5 is a diagram of the mobile device of FIG. 1 in an area.
Figure 6:
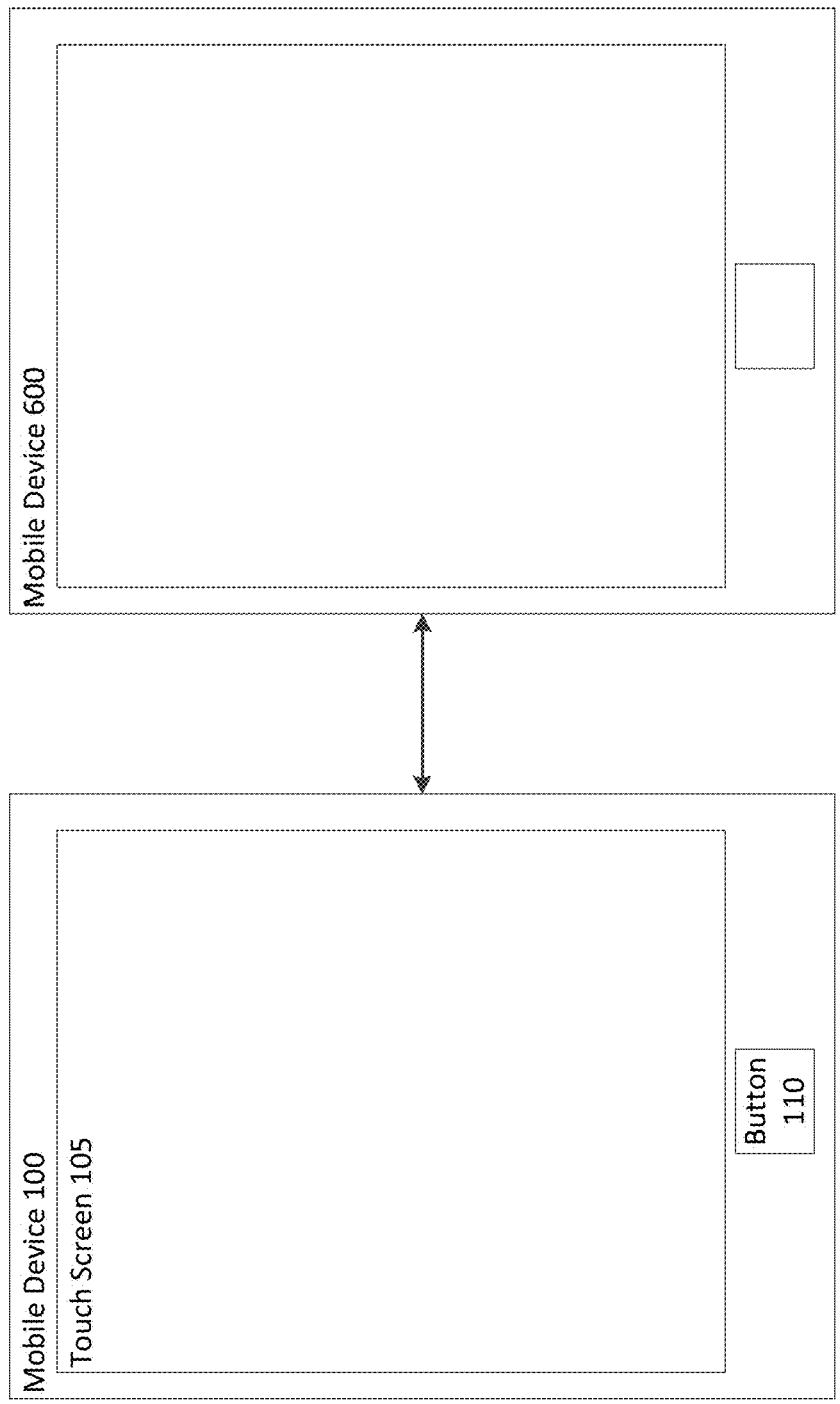
FIG. 6 is a diagram of the mobile device of FIG. 1 communicating with another mobile device.

FIG. 5 illustrates the mobile device 100 in an area 500. The area 500 is a geographical area, for example, a geofence matching a perimeter of a building such as a hospital. In some embodiments, the electronic processor 200 tracks the location of the mobile device 100. In one embodiment, the electronic processor 200 ceases to output the user notification via at least one of the output devices 220 when the electronic processor 200 detects that the mobile device 100 leaves the area 500. The electronic processor 200 also ceases to update the timer 252 and the activity level 270 when the electronic processor 200 detects that the mobile device 100 has left the area 500. If the electronic processor 200 detects that the mobile device 100 enters the area 500, the electronic processor 200 sets the disinfection status 275 of the mobile device 100 to not disinfected and outputs the user notification (for example, periodically) via at least one of the output devices 220.

In some embodiments, the mobile device 100 communicates to the remote server 230 (a cloud server) or another mobile device a time during which the mobile device 100 is in use in the area 500 and the disinfection status 275 is disinfected. (In one example, the mobile device 100 is defined as being in use if the electronic processor 200 receives input from the user a predetermined number of times during a predetermined period.) The mobile device 100 also communicates to the remote server 230 or the other mobile device a time during which the mobile device 100 is in use in the area 500 and the disinfection status 275 is not disinfected. The remote server 230 or the other mobile device establishes a rating for the mobile device 100 based on this information. In other words, the rating is based on 1) the time that the mobile device 100 is in use in the area 500 and the disinfection status 275 is disinfected and 2) the time that the mobile device 100 is in use in the area 500 and the disinfection status 275 is not disinfected. In other embodiments, the mobile device 100, rather than the remote server 230 or the other mobile device, establishes the rating. In one example, the rating allows a hospital administrator to determine mobile devices that are often in use while not disinfected. The hospital administrator can then determine that users of the mobile devices often in use while not disinfected need to receive training on disinfecting mobile devices.

In some embodiments, multiple mobile devices interact with one another. In one example, the mobile device 100, receives a request for information from another mobile device, for example, a mobile device 600. The requested information may include, among other things, the disinfection status 275 of the mobile device 100, whether the mobile device 100 is in use, the time the mobile device 100 is in use in the area 500 and the disinfection status 275 is not disinfected, the time that the mobile device 100 is in use in the area 500 and the disinfection status 275 is disinfected, an identifier of the mobile device 100, and an identification of the person responsible for the mobile device 100. In some embodiments, the mobile device 600 sends the request for information to mobile devices within a predetermined radius, for example, 100 feet, of the mobile device 600. In other embodiments, the mobile device 600 sends the request for information to mobile devices in a field of view of a camera of the mobile device 600. The mobile device 100 verifies the credentials of the mobile device 600 requesting information. For example, the mobile device 600 sends an identification code to the mobile device 100 and the mobile device 100 accesses the remote server 230 or a look up table stored in memory 205 to verify that it can send the information to mobile device 600. If the mobile device 100 verifies that information can be sent to the mobile device 600, the mobile device 100 sends the requested information to the mobile device 600. In some embodiments, an electronic processor of the mobile device 600 displays, via a display, a description of each of the mobile devices, including the mobile device 100, that sent information to the mobile device 600. For example, the description of the mobile device 100 may include the identification of the mobile device 100, the disinfection status 275 of the mobile device 100, and the name of the person responsible for disinfecting the mobile device 100. In other embodiments, the electronic processor of the mobile device 600 augments the image feed from the camera to create an augmented reality environment. Mobile devices in the image feed that have a disinfection status of not disinfected are marked, for example, by an adjacent image, in the augmented reality environment.

Allowing mobile devices to interact with each other, as described above, gives medical personnel (for example, infection control supervisors and shift nurses) the ability to check the disinfection status of mobile devices from their own mobile device. Using the mobile devices' ability to communicate with one another the medical personnel can quickly check the status of mobile devices in the surrounding area as the medical personnel perform rounds.

Figure 7:
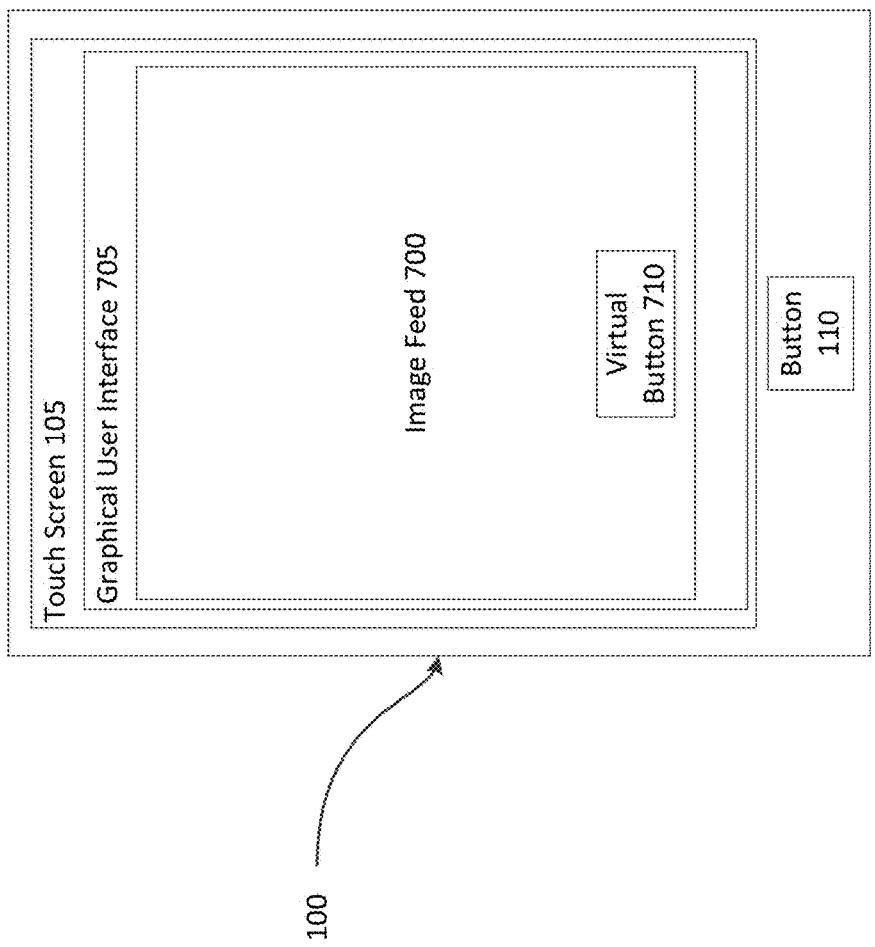
FIG. 7 is a diagram of the mobile device of FIG. 1 displaying an image feed.

FIG. 7 illustrates the mobile device 100 displaying an image feed 700 from the camera 125 within a graphical user interface 705 on the touch screen 105. The electronic processor 200 executes instructions from the graphical user interface generator 245 to generate the graphical user interface 705. Upon receiving an indication that the user wants to use the camera 125 to provide information about the disinfectant, the electronic processor 200 displays the image feed 700 from the camera 125 on the touch screen 105. In some embodiments, the electronic processor 200 automatically detects and processes the information about the disinfectant within the image feed. The information about the disinfectant within the image feed 700 is, for example, a bar code or a unique device identifier (UDI) including the persistence claim of the disinfectant, the threshold time 255 of the disinfectant, the threshold activity level 260 of the disinfectant, or a combination of the foregoing. The bar code or the UDI may be located on the exterior or the interior of the disinfectant's package or on the packaging of a disinfectant wipe. In other embodiments, the user uses the camera 125 to capture an image of the bar code or the UDI by, for example, pressing the button 110 or a virtual button 710. The electronic processor 200 detects and processes the information about the disinfectant within the captured image.

Figure 8:
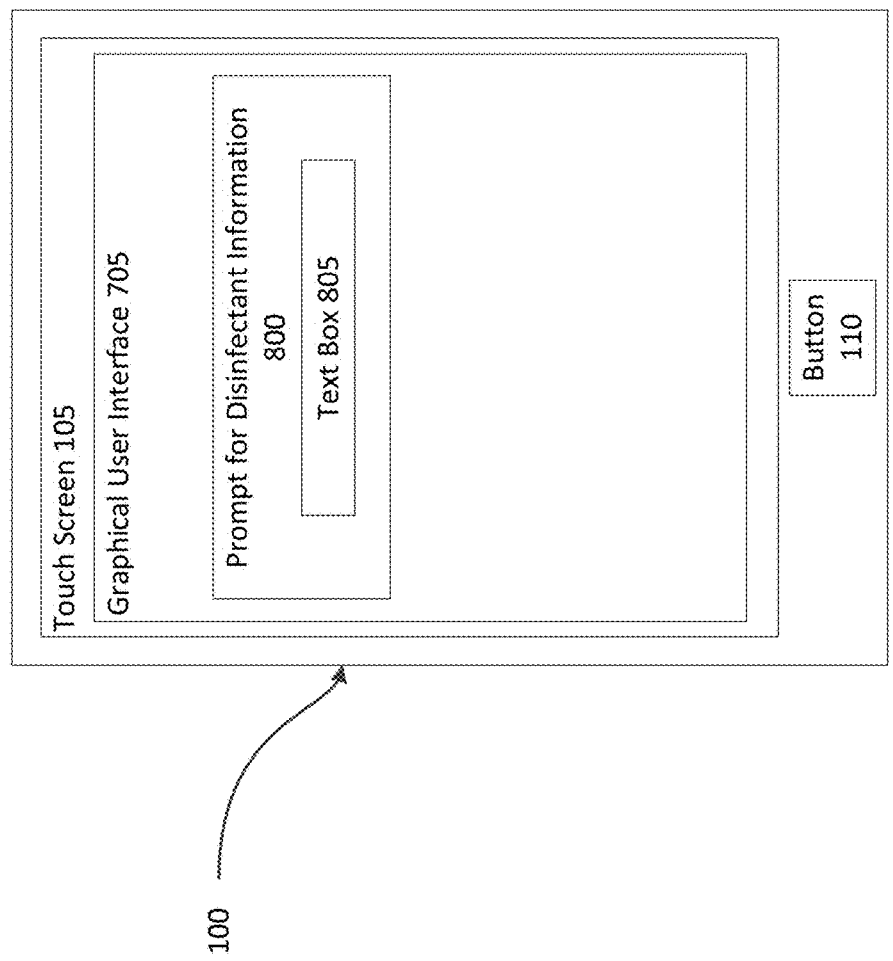
FIG. 8 is a diagram of the mobile device of FIG. 1 displaying a prompt for disinfectant information.

As described above, the camera 125 is one way to obtain and ultimately provide information about the disinfectant to the electronic processor 200. Another way to provide information about the disinfectant is illustrated in FIG. 8. FIG. 8 illustrates the mobile device 100 displaying a prompt 800 for information about the disinfectant within the graphical user interface 705. The electronic processor 200 outputs the prompt 800 via the touch screen 105 upon receiving an indication that the user wants to use the touch screen 105 to provide information about the disinfectant. In some embodiments, the user enters the information about the disinfectant via a text box 805 within the prompt 800. The information about the disinfectant that the user enters via the text box 805 is, for example, a name of the disinfectant, a serial number of the disinfectant, or other unique identifier of the disinfectant.

Figure 9:
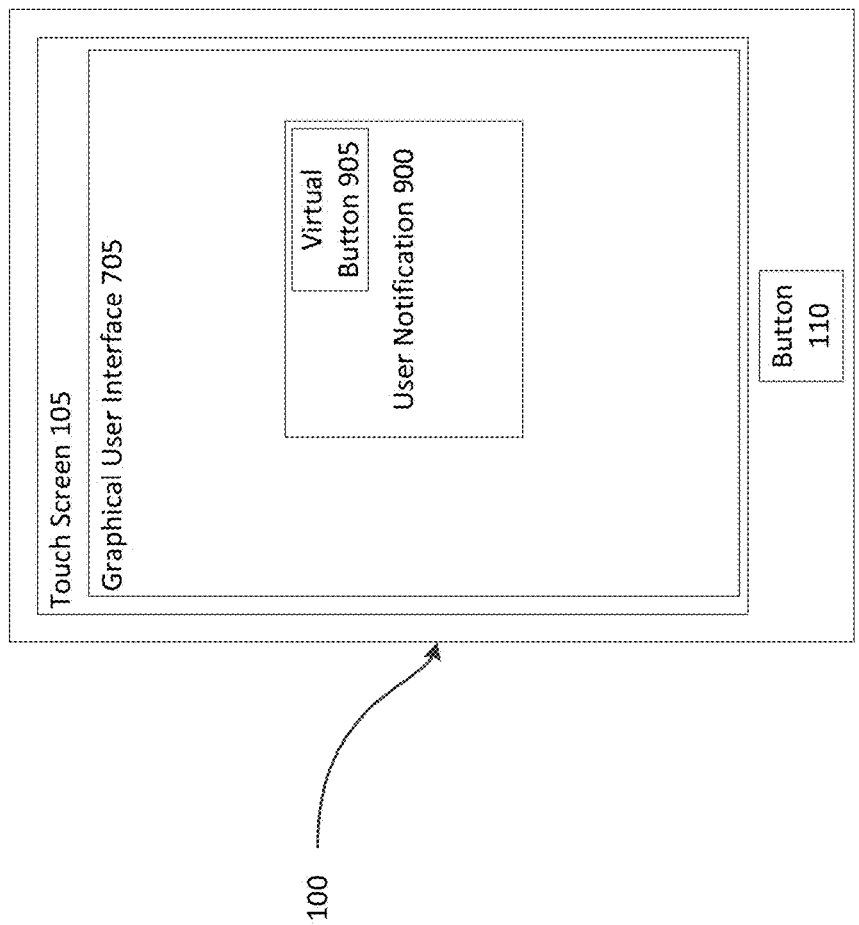
FIG. 9 is a diagram of the mobile device of FIG. 1 displaying a user notification.

FIG. 9 illustrates the mobile device 100 displaying a user notification 900 within the graphical user interface 705 on the touch screen 105. The user notification 900 alerts the user that the mobile device 100 is not disinfected. In some examples, the user is able to close the user notification 900 by touching the button 110 or a virtual button 905. However, in some embodiments, the user notification 900 is redisplayed (for example, periodically) until the electronic processor 200 receives information about the disinfectant. In other examples, the user notification 900 ceases to be displayed on the touch screen 105 a set period of time after it appears on the touch screen 105, but is redisplayed if the electronic processor 200 does not receive information about the disinfectant. In some embodiments, the user notification 900 is redisplayed (for example, periodically) until the electronic processor 200 receives information about the disinfectant and detects the application of the disinfectant.

Various features and advantages are set forth in the following claims.

What is claimed is:

1. A mobile device comprising:
an input device;
an output device; and
an electronic processor connected to the input device and the output device and configured to:
receive, from the input device, information about a disinfectant;
set, based on the information about the disinfectant, a threshold time, a threshold activity level, or both the threshold time and the threshold activity level;
track a passage of time, an activity level, or both; and
output a user notification, via the output device, if the passage of time is greater than or equal to the threshold time, the activity level is greater than or equal to the threshold activity level, or both.

2. The mobile device of claim 1, wherein the information received about the disinfectant is a unique device identifier for the disinfectant, and information stored in a memory of the mobile device includes the threshold time for the disinfectant, the threshold activity level for the disinfectant, or both.

3. The mobile device of claim 1, wherein the information received about the disinfectant includes any of the following: a unique device identifier for the disinfectant, the threshold time for the disinfectant, and the threshold activity level for the disinfectant.

4. The mobile device of claim 1, wherein the activity level is an amount of time that a touch screen of the mobile device is active, an amount of time an accelerometer of the mobile device outputs a value greater than zero, or both.

5. The mobile device of claim 1, wherein the activity level is a number of screen touches.

6. The mobile device of claim 5, wherein the number of screen touches provides information on a removal of disinfectant, an addition of potential contamination, or both.

7. The mobile device of claim 1, wherein the electronic processor is configured to:
track the mobile device's location; and
cease to output the user notification, via the output device, when the mobile device leaves an area.

8. The mobile device of claim 7, wherein the electronic processor is configured to output the user notification, via the output device, when the mobile device enters the area.

9. The mobile device of claim 1, wherein the electronic processor is configured to output the user notification until the electronic processor receives user input, detects an application of the disinfectant to the mobile device, or receives information about a disinfectant.

10. The mobile device of claim 1, wherein a disinfection status of the mobile device is set to disinfected when the electronic processor receives information about the disinfectant.

11. The mobile device of claim 10, wherein the disinfection status is set to not disinfected when the passage of time is greater than or equal to the threshold time, when the activity level is greater than or equal to the threshold activity level, or both.

12. The mobile device of claim 1, wherein the electronic processor is configured to communicate with a remote server, another mobile device, or both,
and to communicate information about a disinfection status of the mobile device, a time period that the mobile device had the disinfection status, or both.

13. The mobile device of claim 1, wherein the electronic processor is configured to set the threshold time, the threshold activity level, or both the threshold time and threshold activity level based on a persistence claim of the disinfectant.

14. The mobile device of claim 1, wherein the input device is a touch screen configured to receive information about the disinfectant and send that information to the electronic processor.

15. The mobile device of claim 1, wherein the output device is a touch screen configured to display the user notification in a graphical user interface.

16. The mobile device of claim 1, wherein the electronic processor is further configured to detect an application of the disinfectant.

17. The mobile device of claim 1, wherein the electronic processor is configured to:
determine, based on the information about the disinfectant, whether the disinfectant has a persistence claim; and
output an error message, via the output device, if the disinfectant does not have a persistence claim.

18. A method for monitoring a disinfection status of a mobile device:
receiving, via an input device, information about a disinfectant;
setting, with an electronic processor, based on the information about the disinfectant, a threshold time, a threshold activity level, or both the threshold time and the threshold activity level;
tracking, with the electronic processor, a passage of time, an activity level, or both; and
outputting a user notification, via an output device, if the passage of time is greater than or equal to the threshold time, the activity level is greater than or equal to the threshold activity level, or both.

19. The method according to claim 18, wherein the information received about the disinfectant is a unique device identifier for the disinfectant, and information stored in a memory of the mobile device includes the threshold time for the disinfectant, the threshold activity level for the disinfectant, or both.

20. The method according to claim 18, wherein the information received about the disinfectant includes any of the following: a unique device identifier for the disinfectant, the threshold time for the disinfectant, and the threshold activity level for the disinfectant.

21. The method according to claim 18, wherein the activity level is an amount of time a touch screen of the mobile device is active, an amount of time an accelerometer of the mobile device outputs a value greater than zero, or both.

22. The method according to claim 18, wherein the activity level is a number of screen touches.

23. The method according to claim 22, wherein the number of screen touches provides information on a removal of disinfectant, an addition of potential contamination, or both.

24. The method according to claim 18, the method further comprising:
   tracking the mobile device's location;
   ceasing to output the user notification, via the output device, when the mobile device leaves an area.

25. The method according to claim 24, wherein the electronic processor is configured to output the user notification, via the output device, when the mobile device enters the area.

26. The method according to claim 18, the method further comprising outputting the user notification until user input is received, an application of the disinfectant is detected, or information about a disinfectant is received.

27. The method according to claim 18, wherein the disinfection status of the mobile device is set to disinfected when the electronic processor receives information about the disinfectant.

28. The method according to claim 18, wherein the disinfection status is set to not disinfected when the passage of time is greater than or equal to the threshold time, when the activity level is greater than or equal to the threshold activity level, or both.

29. The method according to claim 18, the method further comprising communicating with a remote server, another mobile device, or both,
   and communicating information about the disinfection status of the mobile device, a time period that the mobile device had the disinfection status, or both.

30. The mobile device of claim 18, wherein the electronic processor is configured to set the threshold time, the threshold activity level, or both the threshold time and threshold activity level based on a persistence claim of the disinfectant.

31. The method according to claim 18, the method further comprising detecting an application of the disinfectant.

32. The method according to claim 18, the method further comprising:
   determining, based on the information about the disinfectant, whether the disinfectant has a persistence claim; and
   outputting an error message, via the output device, if the disinfectant does not have a persistence claim.

* * * * *